(12) United States Patent
Honda

(10) Patent No.: US 10,631,891 B2
(45) Date of Patent: Apr. 28, 2020

(54) ENERGY TREATMENT DEVICE

(71) Applicant: OLYMPUS CORPORATION, Hachioji-shi, Tokyo (JP)

(72) Inventor: Yoshitaka Honda, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/604,308

(22) Filed: May 24, 2017

(65) Prior Publication Data

US 2017/0252091 A1 Sep. 7, 2017

Related U.S. Application Data

(63) Continuation of application No. PCT/JP2016/063891, filed on May 10, 2016.

(30) Foreign Application Priority Data

Jun. 17, 2015 (JP) ................................. 2015-121628

(51) Int. Cl.
  *A61B 18/14* (2006.01)
  *A61B 17/32* (2006.01)
  (Continued)

(52) U.S. Cl.
  CPC ........ *A61B 17/320092* (2013.01); *A61B 5/01* (2013.01); *A61B 18/1445* (2013.01);
  (Continued)

(58) Field of Classification Search
  CPC .......... A61B 2018/00702; A61B 18/14; A61B 18/1442; A61B 18/1445
  See application file for complete search history.

(56) References Cited

U.S. PATENT DOCUMENTS

2004/0116952 A1 * 6/2004 Sakurai ............... A61B 17/1628
   606/169
2005/0203504 A1 * 9/2005 Wham ............... A61B 18/1442
   606/34
(Continued)

FOREIGN PATENT DOCUMENTS

EP       2510891 A1    10/2012
JP    2000-271137 A    10/2000
(Continued)

OTHER PUBLICATIONS

Dec. 28, 2017 International Preliminary Report on Patentability issued in International Patent Application No. PCT/JP2016/063891.
(Continued)

*Primary Examiner* — Linda C Dvorak
*Assistant Examiner* — Ryan T Clark
(74) *Attorney, Agent, or Firm* — Oliff PLC

(57) ABSTRACT

An energy treatment device includes, a first power accumulator which accumulates electric power; a clock generation portion which generates a clock signal based on the electric power; a controller which uses the clock signal to control supply of an energy to be used for treatment at a treatment portion; a trigger portion which generates a trigger signal that permits the clock generation portion and the first power accumulator to be electrically connected so that the controller receives the clock signal; and a switching portion which, in accordance with a presence/absence of the trigger signal at the trigger portion, switches between a connected state, where the clock generation portion and the first power accumulator are electrically connected, and a disconnected state, where the clock generation portion and the first power accumulator are electrically separated.

13 Claims, 8 Drawing Sheets

(51) Int. Cl.
*A61B 5/01* (2006.01)
*A61B 17/00* (2006.01)
*A61B 90/00* (2016.01)
*A61B 18/00* (2006.01)

(52) U.S. Cl.
CPC ..... *A61B 17/32* (2013.01); *A61B 2017/00017* (2013.01); *A61B 2017/00734* (2013.01); *A61B 2017/320095* (2017.08); *A61B 2018/00589* (2013.01); *A61B 2018/00601* (2013.01); *A61B 2018/00702* (2013.01); *A61B 2018/00815* (2013.01); *A61B 2018/00821* (2013.01); *A61B 2018/00994* (2013.01); *A61B 2090/065* (2016.02); *A61B 2560/028* (2013.01); *A61B 2560/0209* (2013.01); *A61B 2562/0271* (2013.01)

(56) References Cited

U.S. PATENT DOCUMENTS

| | | | |
|---|---|---|---|
| 2012/0078278 A1 | 3/2012 | Bales, Jr. et al. | |
| 2012/0116366 A1* | 5/2012 | Houser | A61B 17/00234 606/1 |
| 2012/0191076 A1* | 7/2012 | Voegele | A61B 17/07207 606/1 |
| 2015/0157354 A1 | 6/2015 | Bales, Jr. et al. | |
| 2016/0045247 A1* | 2/2016 | Heim | A61B 90/30 606/45 |
| 2016/0324537 A1* | 11/2016 | Green | A61B 17/320068 |
| 2018/0168758 A1* | 6/2018 | Lutzow | A61B 34/30 |

FOREIGN PATENT DOCUMENTS

| | | |
|---|---|---|
| JP | 2000-287986 A | 10/2000 |
| JP | 2006-068537 A | 3/2006 |
| JP | 2009-220213 A | 10/2009 |
| JP | 2012-223582 A | 11/2012 |
| JP | 2013-513350 A | 4/2013 |
| JP | 2014-500062 A | 1/2014 |
| WO | 2014/210136 A1 | 12/2014 |

OTHER PUBLICATIONS

Jul. 26, 2016 International Search Report issued in International Patent Application No. PCT/JP2016/063891.

Jan. 3, 2019 Search Report issued in European Patent Application No. 16811347.0.

Feb. 1, 2019 Office Action issued in Chinese Patent Application No. 201680004159.8.

\* cited by examiner

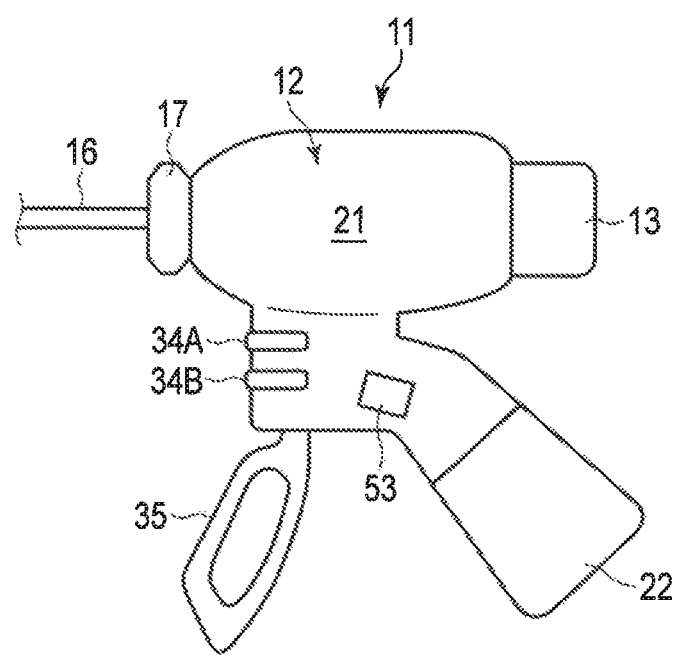
F I G. 13

ENERGY TREATMENT DEVICE

CROSS-REFERENCE TO RELATED APPLICATIONS

This application is a Continuation application of PCT Application No. PCT/JP2016/063891, filed May 10, 2016 and based upon and claiming the benefit of priority from prior Japanese Patent Application No. 2015-121628, filed Jun. 17, 2015, the entire contents of all of which are incorporated herein by reference.

BACKGROUND OF THE INVENTION

1. Field of the Invention

The present invention relates to an energy treatment device that performs treatment on biotissue.

2. Description of the Related Art

Jpn. Pat. Appln. KOKAI Publication No. 2012-223582 (Patent Literature 1) discloses a battery assembly for a surgical device, in which a control circuit selectively allows or disallows power to be supplied from a battery to the surgical device based on certain information. In this battery assembly for a surgical device, prior to activation, both a battery controller and an oscillator are in a standby state. When a user pushes a button, they are activated from the standby state. Signals start to be exchanged between the battery controller and the oscillator. The battery controller supplies electric power from the battery to the oscillator.

SUMMARY OF INVENTION

An energy treatment device of a certain aspect of the present invention includes a first power accumulator which accumulates electric power, a clock generation portion which generates a clock signal based on the electric power, a controller which uses the clock signal to control supply of energy to be used for treatment at a treatment portion, a trigger portion which generates a trigger signal that permits the clock generation portion and the first power accumulator to be electrically connected so that the controller can receive the clock signal, and a switching portion which switches between a connected state, in which the clock generation portion and the first power accumulator are electrically connected, and a disconnected state in which the clock generation portion and the first power accumulator are electrically separated, in accordance with the presence/absence of the trigger signal at the trigger portion.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 13 is a schematic diagram showing an energy treatment device according to a first modified example of the third embodiment.

DESCRIPTION OF EMBODIMENTS

First Embodiment

A first embodiment of an energy treatment device of the present invention will be explained with reference to FIGS. 1 to 4. An energy treatment device 11 (a hand piece) of the following embodiment is suitably used in a state of being physically separated from a power source device (a power source box) connected to a power source of a building, that is, in a cordless state. However, it is also possible to be used in a state of being connected to the power source device via a cord. Here, the energy treatment device 11 will be explained by referring to one of the two directions in parallel with a central axis C of a housing main body 21 as a distal end direction C1, and the opposite of the distal end direction as a proximal end direction C2.

Figure 1:
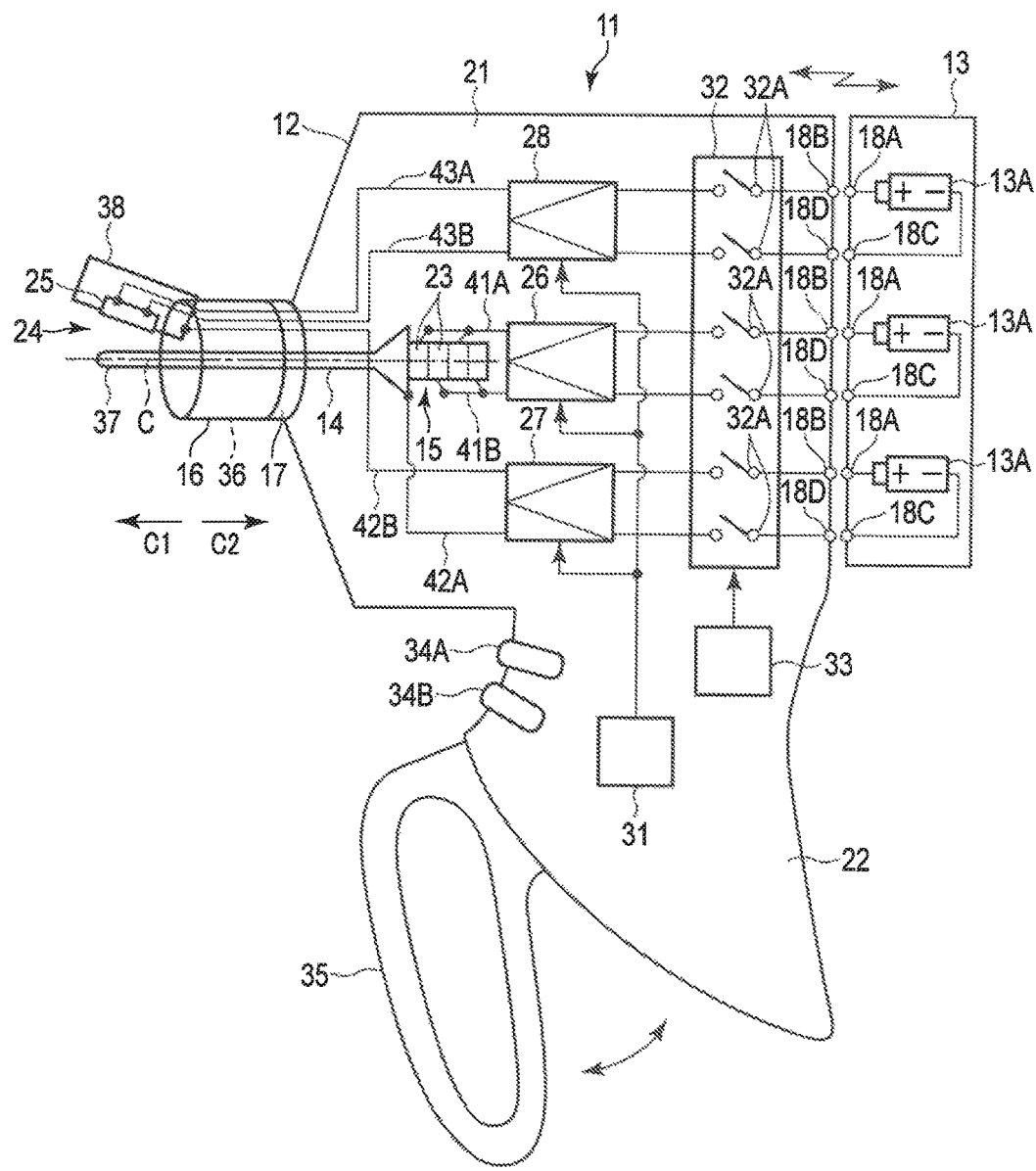
FIG. 1 is a schematic diagram showing an energy treatment device according to a first embodiment.

As shown in FIG. 1, the energy treatment device 11 comprises a housing 12 which can be held by hand by an operator, a battery unit 13 (a first power accumulator) which is detachably attached to the housing 12, a rod-like vibration transmitting portion 14, a part of which is accommodated in the housing 12, and a distal side part of the vibration transmitting portion 14 is protruded outside the housing 12, an ultrasonic transducer 15 which is fixed on a proximal side of the vibration transmitting portion 14, a cylindrical sheath 16 which is revolvably attached to the housing 12 and that covers the vibration transmitting portion 14, and a revolving knob 17 fixed to the sheath 16.

The housing 12 comprises a housing main body 21, and a grip 22 (fixed handle) that extends from the housing main body 21 towards a direction intersecting the central axis C of the housing main body 21.

The battery unit 13 (the first power accumulator) comprises a plurality of (for example, three) batteries 13A. However, the number of batteries of batteries 13A is not limited to three, and may also be one. By attaching the battery unit 13 to the housing 12, an electric contact point 18A comes in contact with an electric contact point 18B, and an electric contact point 18C comes in contact with an electric contact point 18D. This allows the battery 13A to be electrically connected to a switch portion 32 mentioned later on.

The vibration transmitting portion 14 is formed of a conductive material. The ultrasonic transducer 15 includes a plurality of piezoelectric elements 23 that convert an electric energy (alternating-current power) into ultrasonic vibration. The sheath 16 is cylindrically formed by a conductive metal material. In FIG. 1, the length of the sheath 16 is shortened and shown; however, the length is actually several times to several tens of times longer than the length shown in the drawing. The revolving knob 17 is revolvable about the central axis C (about the axis) with respect to the housing 12.

Figure 2:
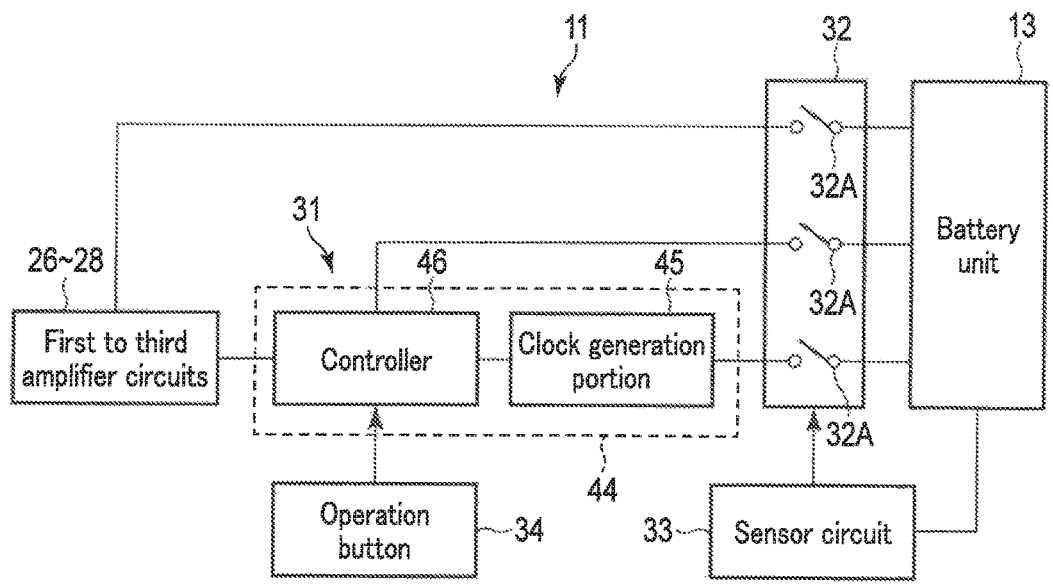
FIG. 2 is a schematic diagram showing configurations of a control circuit and a sensor circuit of the energy treatment device shown in FIG. 1.

As shown in FIG. 1 and FIG. 2, the energy treatment device 11 comprises: a treatment portion 24 (an end effector) provided on the distal side of the vibration transmitting portion 14 (the distal side of the sheath 16); a heater 25 (a heating element) provided on a second gripping piece 38, explained later on, of the treatment portion 24; first to third amplifier circuits 26 to 28 capable of amplifying electric current for providing various energies to the treatment portion 24; a control circuit 31 which controls the first to third amplifier circuits 26 to 28; a switch portion 32 (a switching portion) interposed between a clock generation portion 45, explained later on, in the control circuit 31 and the battery unit 13; a sensor circuit 33 capable of detecting whether the energy treatment device 11 is in a used state or an unused state; a plurality of operation buttons 34 for an operator to switch an output of each of the various energies between on/off with respect to the treatment portion 24; a handle 35 (a movable handle) rotatably provided with respect to the housing 12; and a cylindrical movable pipe 36 provided on the inner side of the sheath 16.

The treatment portion 24 comprises a first gripping piece 37 provided on the distal side of the vibration transmitting portion 14, and the second gripping piece 38 (a jaw) rotatably attached to the distal portion of the sheath 16. By rotating the second gripping piece 38, the first gripping piece 37 and the second gripping piece 38 can be open or closed with respect to each other. In the present embodiment, the end effector that uses a supplied treatment energy to treat a treatment target of a biotissue, etc. is configured by the first gripping piece 37 and the second gripping piece 38. Upon treatment, the treatment target (biotissue, etc.) is gripped between the first gripping piece 37 and the second gripping piece 38, and the treatment energy is applied. By revolving the revolving knob 17, the sheath 16, the vibration transmitting portion 14 (the first gripping piece 37), the ultrasonic transducer 15, and the second gripping piece 38 can be revolved about the central axis C with respect to the housing 12.

The heater 25 is capable of converting an electric energy (direct-current power) into a heat energy. By rotating the handle 35 with respect to the housing 12, an open/close operation of the treatment portion 24 mentioned above can be performed. That is, the handle 35 is rotated to move the movable pipe 36 along the central axis C of the sheath 16, thereby causing the second gripping piece 38 to perform an open/close motion.

As shown in FIG. 1, the first amplifier circuit 26 for ultrasonic energy is electrically connected to the ultrasonic transducer 15 via electric passages 41A and 41B, and is capable of supplying a suitably amplified electric current to the ultrasonic transducer 15. The second amplifier circuit 27 for high-frequency energy is electrically connected to the vibration transmitting portion 14 via an electric passage 42A, and is electrically connected to the second gripping piece 38 via an electric passage 42B. The second amplifier circuit 27 is capable of supplying a suitably amplified electric current (a high-frequency current) to the vibration transmitting portion 14 and the second gripping piece 38. The third amplifier circuit 28 for heat energy is electrically connected to the heater 25 via electric passages 43A and 43B, and is capable of supplying a suitably amplified electric current to the heater 25.

The control circuit 31 comprises a CPU 44, a ROM, and a RAM, etc., and a motherboard (a substrate) that mounts them and has wirings formed thereon to connect each other. As shown in FIG. 2, the CPU 44 comprises a clock generation portion 45 that generates a clock signal, and a controller 46 (a main controller) that is activated by the clock signal generated by the clock generation portion 45, and mainly controls the first to third amplifier circuits 26 to 28.

The controller 46 is capable of controlling the first to third amplifier circuits 26 to 28 to control the supply of energy used for treatment at the treatment portion 24. The switch portion 32 is comprised of a general relay circuit. The switch portion 32 is preferably configured by, for example, a semiconductor relay (a photo MOS relay, a photocoupler, a FET, a transistor gate); however, it may also be configured by a mechanical relay circuit.

The switch portion 32 (the switching portion) is provided on the motherboard of the control circuit 31. Under the control of the sensor circuit 33, the switch portion 32 can be switched between a connected state in which the clock generation portion 45 and the battery unit 13 are electrically connected, and a disconnected state in which the clock generation portion 45 and the battery unit 13 are electrically separated.

Figure 4:
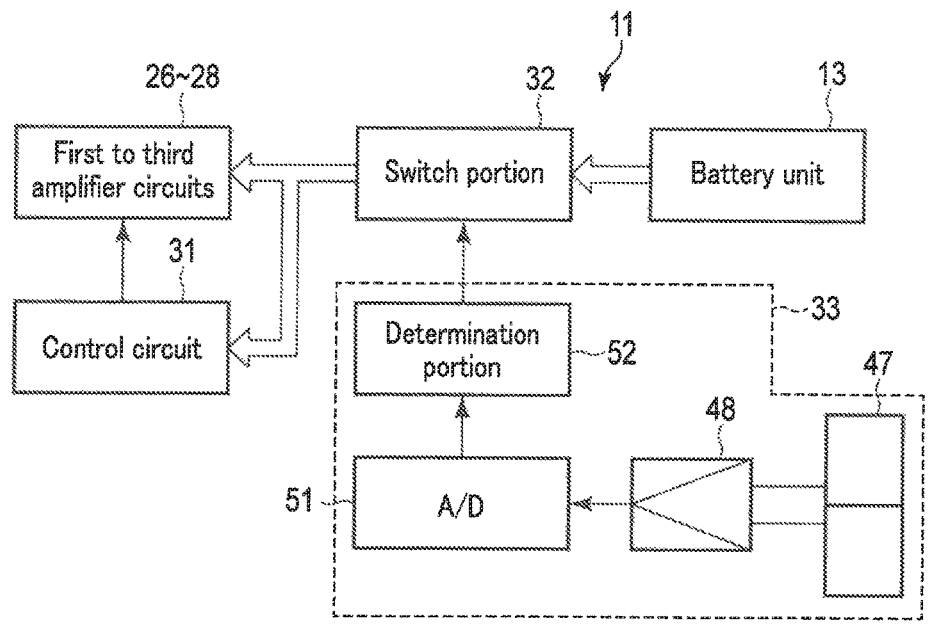
FIG. 4 is a block diagram explaining a configuration of the sensor circuit shown in FIG. 2.

As shown in FIG. 4, the sensor circuit 33 comprises a sensor 47 for detecting the state of the energy treatment device 11, an amplifier 48 for amplifying a detection signal of the sensor 47, an A/D converter 51 for performing analog-to-digital conversion, a determination portion 52 for determining a used state and an unused state of the energy treatment device 11 based on a signal from the A/D converter 51, and a sub-substrate mounting these parts (portions) and upon which wirings electrically connecting these portions are formed. In the present embodiment, the sensor circuit 33 is an example of a trigger portion that generates a trigger signal for permitting the clock generation portion 45 and the battery unit 13 (the first power accumulator) to be electrically connected. In the present embodiment, as shown in FIG. 2, the sensor circuit 33 receives electric power from the battery unit 13.

Figure 3:
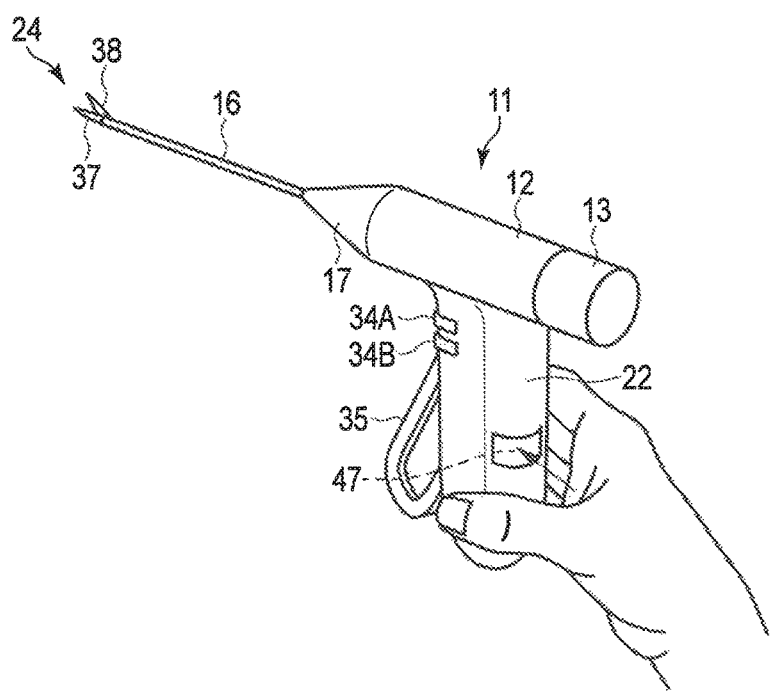
FIG. 3 is a perspective view explaining a position of a sensor of the energy treatment device shown in FIG. 1.

The sensor 47 is provided in contact with an inner surface of a portion that configures the grip 22 (the fixed handle) of the housing 12. The sensor 47 is configured by a thermocouple, and, as shown in FIG. 3, is capable of detecting through the housing the body temperature (heat) of a hand of an operator who is gripping the energy treatment device 11.

As shown in FIG. 4, the determination portion 52 (a computing portion) is configured by one of a microcomputer (a single chip microcomputer), a DSP, and an FPGA, etc., and stores therein threshold information (temperature information, a reference value) which is set at around a body temperature of a human. The determination portion 52 is driven by a smaller number of clocks than the number of clocks (a clock frequency) of the clock generation portion 45. When an operator grips the energy treatment device 11 (the hand piece), an electromotive voltage of different voltages is generated depending on the rise in temperature. The determination portion 52 determines data (voltage information) acquired via the A/D converter 51, and, based on the determination result, controls the switching of the switch portion 32 between a connected state and a disconnected state by a trigger signal mentioned later on.

An operation button 34A corresponds to an incision mode for incising or ablating a biotissue. An operation button 34B corresponds to a coagulation mode for coagulating a biotissue. When the operator operates the operation button 34A or 34B, the controller 46 controls the first to third amplifier circuits 26 to 28 to allow an energy suitable for each mode to be provided to the treatment portion 24. In such case, the controller 46 controls the first amplifier circuit 26, and the first amplifier circuit 26 converts the electric energy (the direct-current power) supplied from the battery unit 13 into an electric energy (alternating-current power) that generates ultrasonic vibration. The electric energy supplied from the first amplifier circuit 26 is supplied to the ultrasonic transducer 15, at which ultrasonic vibration is generated. The ultrasonic vibration is transmitted to the first gripping piece 37 of the treatment portion 24 through the vibration transmitting portion 14 as a treatment energy.

The controller 46 controls the second amplifier circuit 27, and the second amplifier circuit 27 converts the electric energy (the direct-current power) supplied from the battery unit 13 into a high-frequency electric energy (alternating-current power). The high-frequency electric energy supplied from the second amplifier circuit 27 is supplied to the first gripping piece 37 of the treatment portion 24 via the electric passage 42A, as well as the second gripping piece 38 of the treatment portion 24 via an electric passage 42B. The high-frequency electric energy supplied to the first gripping piece 37 and the second gripping piece 38 as a treatment energy allows the first gripping piece 37 and the second gripping piece 38 to function as electrodes (bipolar electrodes) having different potentials from each other.

Furthermore, the controller 46 controls the third amplifier circuit 28 so that the third amplifier circuit 28 converts the electric energy (the direct-current power) supplied from the battery unit 13 into an electric energy (direct-current power) that generates heat. The electric energy supplied from the third amplifier circuit 28 is supplied to a heater via the electric passages 42A and 42B, and heat (treatment energy) is generated at the heater.

In the present embodiment, as the treatment energy supplied to the treatment portion 24, an ultrasonic vibration (an electrical energy generating vibration), a high-frequency electric energy, and heat (an electrical energy generating heat) can be generated. However, it may also be that one or two items among the ultrasonic vibration, the high-frequency electric energy, and the heat be generated as the treatment energy. Furthermore, an energy different from the ultrasonic vibration, the high-frequency electric energy, and the heat may also be generated from the electric energy as the treatment energy, and supplied to the treatment portion 24.

In the following, with reference to FIG. 1 to FIG. 4, an operation of the energy treatment device 11 of the present embodiment will be explained. The operator is capable of using the energy treatment device 11 to perform treatment on a treatment target region. That is, in a state where the housing 12 is gripped by the operator, when the operator clutches the treatment target with the treatment portion 24 by operating the handle 35 and operates the operation button 34A in such state, an energy in a mode suitable for incising the biotissue is provided to the treatment portion 24. When the operation button 34B is operated, an energy in a mode suitable for coagulating the biotissue is provided to the treatment portion 24.

Specifically, the electric power supplied from the battery unit 13 is supplied to the first to third amplifier circuits 26 to 28 via the switch portion 32 under the control of the control circuit 31, is converted into a suitable electric energy at each of the first to third amplifier circuits 26 to 28, and is output from the treatment portion 24 as the ultrasonic energy, the high-frequency energy, and the heat energy. In the used state, the switch portion 32 is in a connected state, in which the battery unit 13 and the control circuit 31 or the first to third amplifier circuits 26 to 28 are electrically connected. In this connected state, the determination portion 52 of the sensor circuit 33 constantly transmits a trigger signal that permits a connected state to the switch portion 32 at regular intervals. The trigger signal can control the connection and disconnection of the switch portion 32.

In a case where the operator completes the treatment, or temporarily stops the treatment, and the energy treatment device 11 is away from the operator's hand and placed on a work table, the temperature of the housing 12 (the grip 22) near the sensor 47 gradually decreases. As shown in FIG. 4, the sensor 47 senses the temperature of the housing 12 and transmits temperature information to the determination portion 52. The determination portion 52 compares the temperature information with the threshold information stored therein, and, in a case where the housing 12 near the sensor 47 is determined to have decreased lower than the temperature of a human body, controls the switch portion 32 to switch the connection between the battery unit 13 and the control circuit 31, and the connection between the battery unit 13 and the first to third amplifier circuits 28 from the connected state to a disconnected state. Specifically, the determination portion 52 stops transmitting the trigger signal transmitted at regular intervals when in the connected state. In this state, the energy treatment device 11 enters a power-saving mode (a standby mode) which suppresses power consumption. Only the sensor circuit 33 maintains a connected state with the battery unit 13 and receives electric power supply from the battery unit 13.

In the power-saving mode, the determination portion 52 of the sensor circuit 33 is driven by a significantly smaller number of clocks than the number of clocks of the clock generation portion 45 of the control circuit 31. Therefore, in the power-saving mode, electric power is not consumed at the control circuit 31 or the first to third amplifier circuits 28, and the electric power consumption of the entire energy treatment device 11 is reduced.

In a case where the operator grips the energy treatment device 11 again when the energy treatment device 11 is in the power-saving mode, as shown in FIG. 4, the sensor 47 senses the temperature of the operator and sends the temperature information to the determination portion 52. In the case where the determination portion 52 determines that the treatment has resumed by comparing the temperature information and the threshold information, the determination portion 52 transmits the trigger signal to control the switch portion 32, and switches all of the switches 32A included in the switch portion 32 from the disconnected state to a connected state (refer to FIG. 1 and FIG. 2). This allows the electric power to be supplied to the control circuit 31, and validates the push operation of the operation button 34. After having gone through the above processes, the energy treatment device 11 transitions to an activation mode, in which the energy treatment device 11 is fully activated. In the activation mode, in the same manner as above, the operator is capable of operating the handle 35 or the operation button 34 to perform a desired treatment. In the activation mode, the determination portion 52 transmits a trigger signal to the switch portion 32 at regular intervals.

According to the first embodiment, an energy treatment device 11 comprises a first power accumulator which accumulates electric power, a clock generation portion 45 which generates a clock signal based on the power, a controller 46 which uses the clock signal to control supply of energy to be used for treatment at a treatment portion 24, a trigger portion which generates a trigger signal that permits the clock generation portion 45 and the first power accumulator to be electrically connected so that the controller 46 can receive the clock signal, and a switching portion which switches between a connected state in which the clock generation portion 45 and the first power accumulator are electrically connected, and a disconnected state in which the clock generation portion 45 and the first power accumulator are electrically separated, in accordance with the presence/absence of the trigger signal at the trigger portion.

According to this configuration, the trigger portion controls the switching portion to switch to the disconnected state, thereby stopping the clock signal from being generated at the clock generation portion 45 and the controller 46 from being driven. Therefore, the electric power used in the energy treatment device 11 can be reduced.

The energy treatment device 11 comprises the operation button 34 for turning ON/OFF the supply of energy to be used for treatment at the treatment portion 24. The operation with respect to the operation button 34 becomes valid after the first power accumulator and the clock generation portion 45 are electrically connected by the switching portion. According to this configuration, the controller 46, which is a portion receiving the operation of the operation button 34, can be prevented from unnecessary consumption of the standby power. Therefore, a power-saving energy treatment device 11 that prevents the electric energy of the battery unit from being gradually exhausted over time can be provided.

The switching portion switches to the disconnected state in a case where the trigger signal is not generated from the trigger portion, and switches to the connected state in a case where the trigger signal is generated from the trigger portion.

According to this configuration, in an unused state, etc. in which the energy treatment device 11 is not used, the connection between the first power accumulator and the clock generation portion 45 can be automatically cut off, and the electric power consumed at the clock generation portion 45 and the controller 46 can be made to be zero. Therefore, a power-saving energy treatment device 11 can be provided.

The trigger portion comprises the sensor 47 and the determination portion 52 which determines the used state or the unused state based on the detection result detected at the sensor 47, and generates the trigger signal when in the used state.

This configuration allows the switching portion to become a disconnected state when in the unused state, and can prevent the clock signal from being generated at the clock generation portion 45 when in the unused state. Therefore, power-saving of the energy treatment device 11 can be realized.

The trigger portion is driven by a smaller number of clocks than the number of clocks of the clock generation portion 45. According to this configuration, the electric power consumed at the trigger portion can be made lower than the electric power consumed at the clock generation portion 45 and the controller 46, thereby, realizing power-saving of the energy treatment device 11.

In the present embodiment, in the case where the operator completes the treatment or temporarily stops the treatment, the sensor circuit 33 makes transitions from the activation mode to the power-saving mode. However, the control from the control circuit 31 may transition the switch portion 32 to the disconnected state (the power-saving mode) after a lapse of a predetermined time from when the output of the energy was last made, by, for example, one of the ultrasonic wave, the high frequency, and the heat energy. In such case, as in a first modified example of a third embodiment mentioned later on, it is desirable to provide a second operation button 53 (an activation switch) to the energy treatment device 11 for allowing a forced transition from the power-saving mode to the activation mode. The second operation button 53 will allow the operator to perform transition from the power-saving mode to the activation mode when necessary, and to output various energies to the treatment portion 24.

(First Modified Example of First Embodiment)

Figure 5:
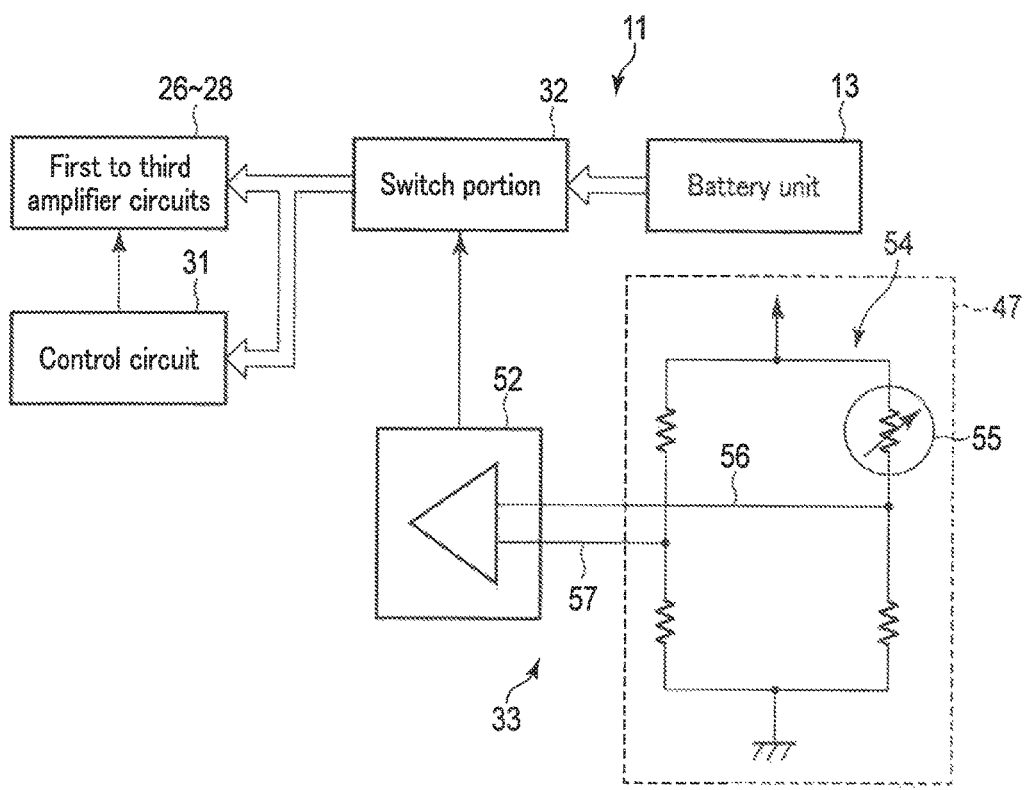
FIG. 5 is a block diagram showing a configuration of a sensor circuit of an energy treatment device according to a first modified example of the first embodiment.

With reference to FIG. 5, a first modified example of the energy treatment device of the first embodiment will be explained. In an energy treatment device 11 of the first modified example, the configuration of a sensor circuit 33 differs from that of the first embodiment. The other parts are identical to the first embodiment. Therefore, mainly the parts different from those of the first embodiment will be explained, and illustrations or explanations of the parts identical to those of the first embodiment will be omitted.

The sensor circuit 33 comprises a sensor 47 for detecting the state of the energy treatment device 11, a determination portion 52 for determining a used state and an unused state of the energy treatment device 11 based on a detection signal of the sensor 47, and a sub-substrate mounting these parts (portions) and having wirings formed thereon for electrically connecting these portions. The sensor 47 comprises a bridge circuit 54 and a thermistor 55 provided on a part of the bridge circuit 54.

The sensor 47 is provided at a position on a grip 22 (a fixed handle), in a manner that contacts an inner surface of a housing 12 configuring the grip 22. The thermistor 55 is a resistor whose resistance value changes depending on the temperature, and can be utilized as a temperature detector. The sensor 47 configured by the thermistor 55 is capable of detecting a body temperature of an operator gripping the energy treatment device 11 via the housing 12.

The determination portion 52 is configured by a comparator. Meanwhile, a switch portion 32 is connected to the determination portion 52, and is capable, for example, of electrically connecting a clock generation portion 45 and a battery unit 13 when an output logic from the determination portion 52 is ON, bringing them to a connected state. When, for example, the output logic from the comparator is OFF, the switch portion 32 is capable of electrically disconnecting the clock generation portion 45 and the battery unit 13, making them a disconnected state. The combination of the output logic of the determination portion 52 (the comparator) and the connected state of the switch portion 32 is an example. Therefore, the switch portion 32 may, of course, be in a connected state when the output logic of the determination portion 52 is OFF.

The thermistor 55 of the bridge circuit 54 and the determination portion 52 are connected by a first wiring 56, and an opposite side of the thermistor 55 of the bridge circuit 54 and the determination portion 52 are connected by the a second wiring 57.

In the present embodiment, the sensor circuit 33 is an example of a trigger portion that generates a trigger signal for permitting the clock generation portion 45 and the battery unit 13 (a first power accumulator) to be electrically connected. In the present embodiment, the sensor circuit 33 receives electric power supply from the battery unit 13.

Next, the operation of the energy treatment device 11 of the present modified example will be explained. The operator is capable of performing treatment on a treatment target region using the energy treatment device 11. That is, in a state where the housing 12 is gripped by the operator, when the treatment target is clutched with the treatment portion 24 by operating a handle 35, and an operation button 34A or an operation button 34B is operated in this state, an energy suitable for each mode is provided to the treatment portion 24. Specifically, the electric power supplied from the battery unit 13 is supplied to first to third amplifier circuits 26 to 28 via the switch portion 32 under the control of a control circuit 31, is converted into a suitable electric energy at each of the first to third amplifier circuits 26 to 28, and is output from the treatment portion 24 as the ultrasonic energy, the high-frequency energy, and heat energy. That is, in a used state, the switch portion 32 is in a connected state in which the battery unit 13 and the control circuit 31 or the first to third amplifier circuits 26 to 28 are electrically connected. In this connected state, the sensor 47 outputs an electric current to the determination portion 52 so that, for example, a potential on the first wiring 56 side becomes lower than that on the second wiring 57 side. In the above manner, the determination portion 52 of the sensor circuit 33 constantly transmits a trigger signal (an ON output logic) for permitting a connected state to the switch portion 32.

In a case where the operator completes the treatment, or temporarily stops the treatment, and the energy treatment device 11 is away from the operator's hand and placed on a work table, the temperature of the housing 12 (the grip 22) near the sensor 47 gradually decreases. When the temperature of the housing 12 becomes equal to or lower than a certain value, the sensor 47 (the bridge circuit 54 including the thermistor 55) outputs an electric current in which a potential difference between the first wiring 56 and the second wiring 57 is reversed (the potential on the first wiring 56 side being higher than the potential on the second wiring 57 side) to the determination portion 52. Therefore, the output logic of the determination portion 52 is reversed and is turned off (transmission of the trigger signal is stopped). Therefore, the switch portion 32 makes the connection between the battery unit 13 and the control circuit 31, and the connection between the battery unit 13 and the first to third amplifier circuits 26 to 28 to be a disconnected state from the connected state. In this state, the energy treatment device 11 enters a power-saving mode (a standby mode) which suppresses power consumption. Only the sensor circuit 33 is connected to the battery unit 13 and receives electric power supply from the battery unit 13.

In a case where the operator grips the energy treatment device 11 again, and the temperature of the housing 12 becomes equal to or larger than the certain temperature when the energy treatment device 11 is in the power-saving mode, the sensor 47 outputs an electric current in which the potential difference between the first wiring 56 and the second wiring 57 is reversed again (the potential on the first wiring 56 side is lower than the potential of the second wiring 57 side) to the determination portion 52. Therefore, the output logic from the determination portion 52 is reversed again and is turned on (the trigger signal is transmitted), and the switch portion 32 switches all of the switches 32A from the disconnected state to the connected state. Therefore, the electric power is supplied to the control circuit 31, and the operation of the operation button 34 is validated. Therefore, the energy treatment device 11 transitions to an activation mode, in which it is fully activated. In the activation mode, in the same manner as above, the operator is capable of operating the handle 35 or the operation button 34 to perform a desired treatment. In the activation mode, the determination portion 52 constantly transmits the trigger signal (the ON output logic) to the switch portion 32.

According to the present modified example, since the sensor 47 is configured by the bridge circuit 54 including the thermistor 55, and the determination portion 52 is configured by the comparator, the dynamic range of voltage variation can be increased, allowing high sensitivity in detecting that the operator has gripped the energy treatment device 11. Therefore, an energy treatment device 11 which saves power and has favorable responsiveness even in a power-saving mode can be provided. Furthermore, the sensor 47 and the determination portion 52 can be configured by inexpensive parts, enabling production costs of the energy treatment device 11 to be reduced.

(Second Modified Example of First Embodiment)

Figure 6:
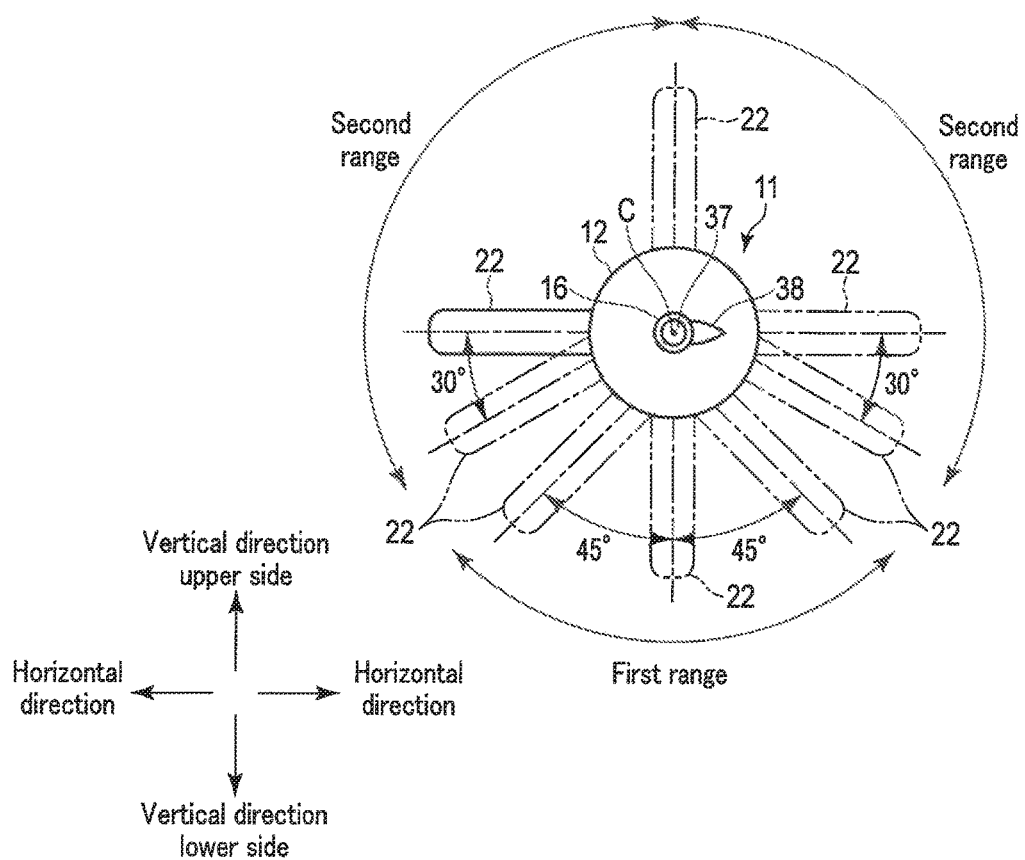
FIG. 6 is a schematic diagram regarding an energy treatment device according to a second modified example of the first embodiment, explaining cases in which a grip position is in a first range and in a second range.

With reference to FIG. 6, a first modified example of the energy treatment device of the first embodiment will be explained. The energy treatment device 11 of the first modified example is different from that of the first embodiment in that a sensor 47 is configured by an inclination sensor. The other parts are identical to the first embodiment. Therefore, mainly the parts different from those of the first embodiment will be explained, and illustrations or explanations of the parts identical to those of the first embodiment will be omitted.

A sensor circuit 33 comprises a sensor 47 for detecting the state of the energy treatment device 11, a determination portion 52 (a computing portion) for determining a used state and an unused state of the energy treatment device 11 based on a signal from the sensor 47, and a sub-substrate mounting these parts (portions) and having wirings formed thereon for electrically connecting these parts. In the present embodiment, the sensor circuit 33 is an example of a trigger portion that generates a trigger signal. In the present embodiment, the sensor circuit 33 receives electric power supply from a battery unit 13.

The sensor 47 is provided somewhere inside the housing 12. The sensor 47 is configured by an inclination sensor 47 (a gyro sensor) and is capable of detecting a current angle (an angle indicating how much a grip 22 has revolved about a central axis C) of the energy treatment device 11. The determination portion 52 is configured by one of a microcomputer (a single chip microcomputer), a DSP, and an FPGA, etc., and stores therein threshold information (threshold conditions) regarding the inclination of the energy treatment device 11. The sensor 47 transmits the current angle (postural information) of the energy treatment device 11 to the determination portion 52 constantly or at regular intervals. The determination portion 52 compares the information with the threshold information. In a case where the postural information obtained from the sensor 47 is within a range (a first range) that is considered as "an energy treatment device used state," the determination portion 52 determines that the energy treatment device 11 is in a used state and is gripped by the operator. On the other hand, in a case where the information is compared to the threshold information, and the postural information obtained by the sensor 47 is within a range (a second range) that is considered as "an energy treatment device unused state," the determination portion 52 determines that the energy treatment device 11 is in an unused state.

In the present embodiment, for example, as shown in FIG. 6, when the grip 22 is within a range of an angle equal to or smaller than 45° from the center of the lower side of a vertical direction, the threshold information is set for the determination portion 52 to determine the range as the first range. Furthermore, when the grip 22 is, for example, within a range of an angle from a position 30° on the lower side than a horizontal direction to a position on the upper side of a vertical direction, the threshold information is set for the determination portion 52 to determine the range as the second range.

The determination portion 52 controls the switch portion 32 to be switched between a connected state and a disconnected state based on the determination result. In the present embodiment, the sensor circuit 33 is an example of a trigger portion that generates a trigger signal for permitting the clock generation portion 45 and the battery unit 13 (the first power accumulator) to be electrically connected. In the present embodiment, the sensor circuit 33 receives electric power supply from the battery unit 13.

Next, the operation of the energy treatment device 11 of the present modified example will be explained. Similar to the first embodiment, by operating the operation button 34A and the operation button 34B, the operator is capable of providing an ultrasonic energy, a high-frequency energy, or a heat energy to the treatment portion 24 to treat the treatment target region. In this used state, the switch portion 32 is in a connected state, in which the battery unit 13 and a control circuit 31, or first to third amplifier circuits 26 to 28 are electrically connected. In this connected state, the sensor 47 sends the postural information of the energy treatment device 11 to the determination portion 52. Therefore, the determination portion 52 determines that the postural information of the energy treatment device 11 is included in the first range and transmits a trigger signal for permitting a connected state to the switch portion 32 at regular intervals.

In the case where the operator completes the treatment or temporarily stops the treatment, and the energy treatment device 11 is placed on a working table, or a part of the energy treatment device 11 is accommodated in a pocket of a drape, the sensor 47 sends the postural information of the energy treatment device 11 to the determination portion 52. Therefore, the determination portion 52 determines that the postural information of the energy treatment device 11 is included in the second range and stops transmitting the trigger signal. Therefore, the switch portion 32 makes the connection between the battery unit 13 and the control circuit 31, and the connection between the battery unit 13 and the first to third amplifier circuits 26 to 28 to be a disconnected state from the connected state. In this state, the energy treatment device 11 enters a power-saving mode (a standby mode) which suppresses power consumption. Only the sensor circuit 33 is connected to the battery unit 13 and receives electric power supply from the battery unit 13.

In the power-saving mode, the determination portion 52 of the sensor circuit 33 is driven by a significantly smaller number of clocks than the number of clocks of the clock generation portion 45 of the control circuit 31.

In a case where the operator grips the energy treatment device 11 again when the energy treatment device is in the power-saving mode, the sensor 47 sends the postural information of the energy treatment device 11 to the determination portion. Due to this, the determination portion 52 determines that the postural information of the energy treatment device 11 is included in the first range and transmits a trigger signal for permitting a connected state to the switch portion 32 at regular intervals. The switch portion 32 switches all of the switches 32A from the disconnected state to a connected state. Therefore, the electric power is supplied to the control circuit 31, and the operation of an operation button 34 is validated. Therefore, the energy treatment device 11 transitions to an activation mode, in which it is fully activated. In the activation mode, in the same manner as above, the operator is capable of operating a handle 35 or the operation button 34 to perform a desired treatment.

According to the present modified example, a power-saving energy treatment device 11 which is capable of preventing standby power to be consumed at the first to third amplifier circuits 26 to 28, the controller 46, and the clock generation portion 45, etc. can be provided.

(Third Modified Example of First Embodiment)

Figure 7:
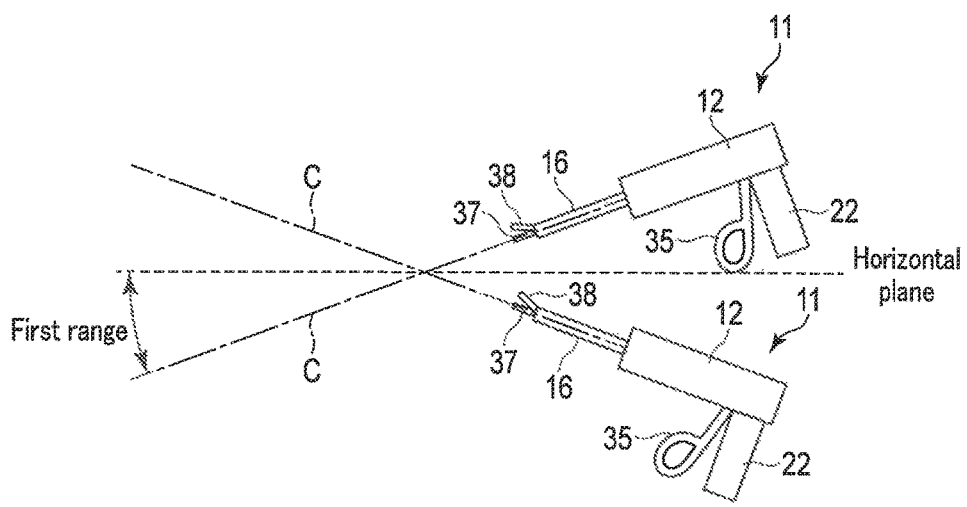
FIG. 7 is a schematic diagram regarding an energy treatment device according to a third modified example of the first embodiment, explaining a state of being in a first range and a state of being in a second range.

With reference to FIG. 7, a third modified example of the energy treatment device 11 of the first embodiment will be explained. The energy treatment device 11 of the third modified example is different from that of the first embodiment in that a sensor 47 configured by an inclination sensor senses the inclination of a central axis C of a vibration transmitting portion 14. The other parts are identical to the first embodiment. Therefore, mainly the parts different from those of the first embodiment will be explained, and illustrations or explanations of the parts identical to those of the first embodiment will be omitted.

A sensor circuit 33 comprises the sensor 47 for detecting the state of the energy treatment device 11 and a determination portion 52 for determining a used state and an unused state of the energy treatment device 11 based on a signal from the sensor 47. In the present embodiment, the sensor circuit 33 is an example of a trigger portion that generates a trigger signal for permitting a clock generation portion 45 and a battery unit 13 (first power accumulator) to be electrically connected. In the present embodiment, the sensor circuit 33 receives electric power supply from the battery unit 13.

The sensor 47 is provided near the vibration transmitting portion 14 inside the housing 12. The sensor 47 is configured by an inclination sensor (a gyro sensor) and is capable of detecting a current inclination of the vibration transmitting portion 14 (a central axis C). The determination portion 52 (a computing portion) is configured by one of a microcomputer (a single chip microcomputer), a DSP, and an FPGA, etc., and stores therein threshold information (threshold conditions) regarding the inclination of the vibration transmitting portion. The sensor 47 transmits the inclination information (postural information) of the vibration transmitting portion 14 to the determination portion 52 constantly or at regular intervals. In a case where the inclination information obtained from the sensor is within a range (a first range) that is considered as "an energy treatment device used state," the determination portion 52 determines that the energy treatment device 11 is gripped by an operator and is in a used state. On the other hand, in a case where the inclination information obtained from the sensor 47 is within a range (a second range) that is considered as "an energy treatment device unused state," the determination portion 52 determines that the energy treatment device 11 is in an unused state.

In the present modified example, the first range is, for example, an angle of depression formed by a distal end direction of the vibration transmitting portion 14 (a central axis C) and a horizontal plane, in which the inclination of the vibration transmitting portion 14 with respect to the horizontal plane can be set, for example, in a range of 00 to 30°, more preferably, in a range of 15° to 30°.

The second range may, for example, be set as a range other than the first range. However, in particular, as in the energy treatment device 11 shown on the lower side in FIG. 7, a range in which an angle formed by the distal end direction of the vibration transmitting portion 14 (central axis C) and the horizontal plane is an angle of elevation that can be set as the second range. The determination portion 52 controls the switch portion 32 to be switched between a connected state and a disconnected state based on the determination result.

Next, the operation of the energy treatment device 11 of the present modified example will be explained. Similar to the first embodiment, by operating operation buttons 34A and 34B, the operator is capable of providing an ultrasonic energy, a high-frequency energy, or a heat energy to a treatment portion 24 to treat a treatment target region. In this used state, the switch portion 32 is in a connected state, in which the battery unit 13 and a control circuit 31 or first to third amplifier circuits 26 to 28 are electrically connected. In this connected state, the sensor 47 sends the inclination information of the energy treatment device 11 to the determination portion 52. Therefore, the determination portion 52 determines that the inclination information of the energy treatment device 11 is included in the first range, and transmits a trigger signal for permitting a connected state to the switch portion 32 at regular intervals.

In the case where the operator completes the treatment or temporarily stops the treatment, and the energy treatment device 11 is placed on a working table, or a part of the energy treatment device 11 is accommodated in a pocket of a drape, the sensor 47 sends the inclination information of the energy treatment device 11 to the determination portion 52. Therefore, the determination portion 52 determines that the inclination information of the energy treatment device 11 is included in the second range and stops transmitting the trigger signal. Therefore, the switch portion 32 makes the connection between the battery unit 13 and the control circuit 31, and the connection between the battery unit 13 and the first to third amplifier circuits 26 to 28 to be a disconnected state from the connected state. In this state, the energy treatment device 11 enters a power-saving mode (a standby mode) which suppresses power consumption. Only the sensor circuit 33 is connected to the battery unit 13 and receives electric power supply from the battery unit 13.

In the power-saving mode, the determination portion 52 of the sensor circuit 33 is driven by a significantly smaller number of clocks than the number of clocks of the clock generation portion 45 of the control circuit 31.

In a case where the operator grips the energy treatment device 11 again when the energy treatment device is in the power-saving mode, the sensor 47 sends the inclination information of the energy treatment device 11 to the determination portion 52. Here, in a case where the determination portion 52 determines that the inclination information of the energy treatment device 11 is included in the first range, a trigger signal to permit a connected state is transmitted to the switch portion 32 at regular intervals. The switch portion 32 switches all of the switches 32A from the disconnected state to a connected state. Therefore, the electric power is supplied to the control circuit 31, and the operation of the operation button 34 is validated. Therefore, the energy treatment device 11 transitions to an activation mode, in which it is fully activated. In the activation mode, in the same manner as above, the operator is capable of operating a handle 35 or the operation button 34 to perform a desired treatment.

According to the present modified example, a power-saving energy treatment device 11 that is capable of preventing standby power from being consumed at the first to third amplifier circuits 26 to 28, the controller 46, and the clock generation portion 45, etc. can be provided.

(Fourth Modified Example of First Embodiment)

A fourth modified example of the energy treatment device of the first embodiment will be explained. An energy treatment device 11 of the fourth modified example is different from that of the first embodiment in that a sensor 47 configured by an acceleration sensor senses a used state of the energy treatment device 11. The other parts are identical to the first embodiment. Therefore, mainly the parts different from those of the first embodiment will be explained, and illustrations or explanations of the parts identical to those of the first embodiment will be omitted.

A sensor circuit 33 comprises a sensor 47 for detecting the state of the energy treatment device 11 and a determination portion 52 for determining a used state and an unused state of the energy treatment device 11 based on a signal from the sensor 47. In the present embodiment, the sensor circuit 33 is an example of a trigger portion that generates a trigger signal for permitting a clock generation portion 45 and a battery unit 13 (a first power accumulator) to be electrically connected. In the present embodiment, the sensor circuit 33 receives electric power supply from the battery unit 13.

The sensor 47 is provided somewhere inside the housing 12. The sensor 47 is configured by an acceleration sensor, and is capable of detecting a current acceleration of the energy treatment device 11. The determination portion 52 (a computing portion) is configured by one of a microcomputer (a single chip microcomputer), a DSP, and an FPGA, etc., and stores therein threshold information (threshold conditions) regarding the acceleration of the energy treatment device 11. The sensor 47 transmits the acceleration information of the energy treatment device 11 to the determination portion constantly or at regular intervals. In a case where the acceleration sensed by the sensor 47 is equal to or higher than a certain threshold, the determination portion 52 determines that the energy treatment device 11 is gripped by an operator, and is in a used state. On the other hand, in a case where the acceleration sensed by the sensor 47 is zero or equal to or lower than the threshold, the determination portion 52 determines that the energy treatment device 11 is not used, and is in an unused state. The determination portion 52 controls a switch portion 32 to be switched between a connected state and a disconnected state based on the determination result.

Next, the operation of the energy treatment device 11 of the present modified example will be explained. Similar to the first embodiment, by operating operation buttons 34A and 34B, the operator is capable of providing an ultrasonic energy, a high-frequency energy, or a heat energy to a treatment portion 24 to treat a treatment target region. In this used state, the switch portion 32 is in a connected state, in which a battery unit 13 and a control circuit 31 or first to third amplifier circuits 26 to 28 are electrically connected. In the connected state, the sensor 47 sends the acceleration information of the energy treatment device 11 to the determination portion 52. Therefore, based on the acceleration information of the energy treatment device 11, the determination portion 52 determines that the energy treatment device 11 is in a used state, and transmits to the switch portion 32 at regular intervals the trigger signal for permitting a connected state.

In the case where the operator completes the treatment or temporarily stops the treatment, and the energy treatment device 11 is placed on a working table, etc., the sensor 47 sends the acceleration information of the energy treatment device 11 to the determination portion 52. Therefore, based on the acceleration information, the determination portion 52 determines that the energy treatment device 11 is in an unused state, and stops transmitting the trigger signal. Therefore, the switch portion 32 makes the connection between the battery unit 13 and the control circuit 31, and the connection between the battery unit 13 and the first to third amplifier circuits 26 to 28 to be a disconnected state from the connected state. In this state, the energy treatment device 11 enters a power-saving mode (a standby mode) which suppresses power consumption. Only the sensor circuit 33 receives electric power supply from the battery unit 13.

In the power-saving mode, the determination portion 52 of the sensor circuit 33 is driven by a significantly smaller number of clocks than the number of clocks of the clock generation portion 45 of the control circuit 31.

In a case where the operator grips the energy treatment device 11 again when the energy treatment device is in the power-saving mode, the sensor 47 sends the acceleration information of the energy treatment device 11 to the determination portion 52. Here, in a case where the energy treatment device 11 is determined as being in a used state based on the acceleration information, the determination portion 52 transmits the trigger signal for permitting a connected state to the switch portion 32 at regular intervals. The switch portion 32 switches all of the switches 32A from the disconnected state to a connected state. Therefore, the electric power is supplied to the control circuit 31, and the operation of an operation button 34 is validated. Therefore, the energy treatment device 11 transitions to an activation mode, in which it is fully activated, which allows the operator to operate a handle 35 and the operation button 34 to perform a desired treatment.

According to the present modified example, a power-saving energy treatment device 11 that is capable of preventing standby power to be consumed at the first to third amplifier circuits 26 to 28, the controller 46, and the clock generation portion 45, etc. can be provided.

(Fifth Modified Example of First Embodiment)

Figure 8:
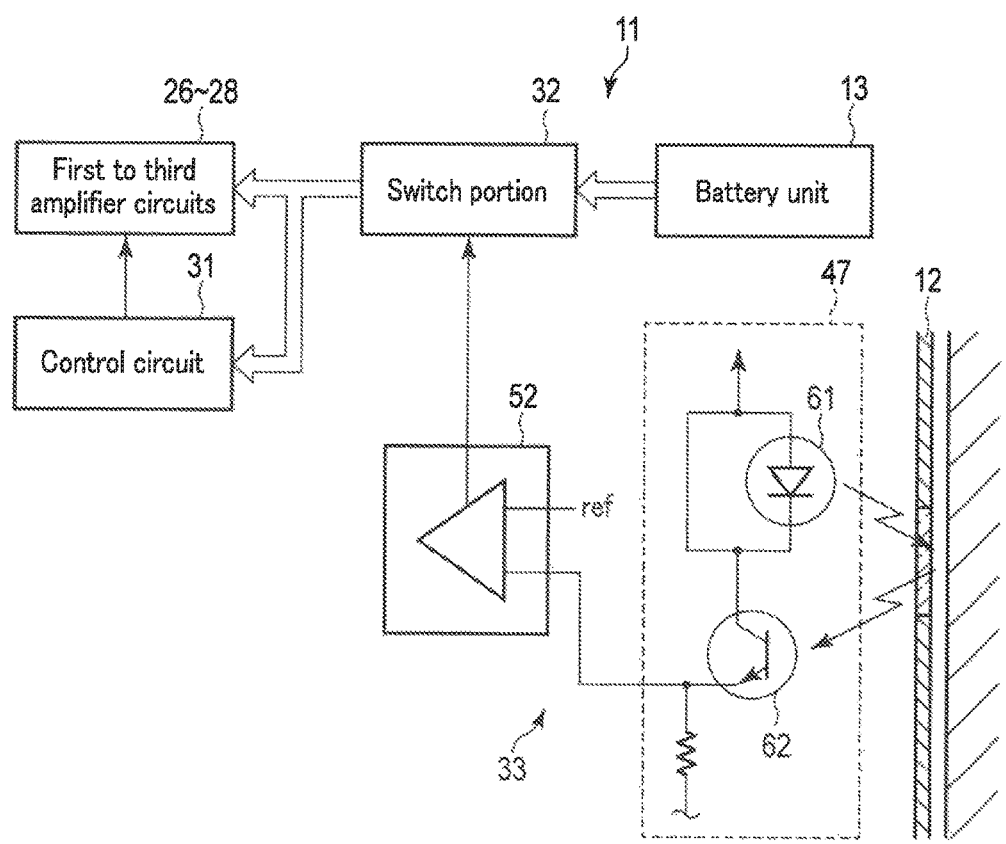
FIG. 8 is a block diagram showing a configuration of a sensor circuit of an energy treatment device according to a fifth modified example of the first embodiment.

With reference to FIG. 8, a fifth modified example of the energy treatment device 11 of the first embodiment will be explained. An energy treatment device 11 of the fifth modified example is different from that of the first embodiment in that a sensor 47 configured by a reflective photo-interrupter senses a gripping hand of an operator. The other parts are identical to the first embodiment. Therefore, mainly the parts different from those of the first embodiment will be explained, and illustrations or explanations of the parts identical to those of the first embodiment will be omitted.

A sensor circuit 33 comprises the sensor 47 for detecting the state of the energy treatment device 11, and a determination portion 52 for determining a used state and an unused state of the energy treatment device 11 based on a signal from the sensor 47. In the present embodiment, the sensor circuit 33 is an example of a trigger portion that generates a trigger signal for permitting a clock generation portion 45 and a battery unit 13 (a first power accumulator) to be electrically connected. In the present embodiment, the sensor circuit 33 receives electric power supply from the battery unit 13.

The sensor 47 is configured by a reflective photo-interrupter (a photo-reflector), and is provided adjacent to a part of a housing 12 (grip 22) formed to have translucency. The sensor 47 includes a light-emitting diode 61 and a phototransistor 62. The sensor 47 is capable of detecting an operator's hand gripping the energy treatment device 11.

The determination portion 52 is configured by a comparator. One of the input terminals of the determination portion 52 and the sensor 47 are connected by a first wiring 56. The other input terminal of the determination portion 52 is connected to a second wiring 57. To the other input terminal, a voltage to be a reference value is added from a power source side via the second wiring 57.

A switch portion 32 is connected to the determination portion 52, and when, for example, an output logic from the determination portion 52 is ON, is capable of electrically connecting a clock generation portion 45 and a battery unit 13, bringing them into a connected state. When, for example, the output logic from the determination portion 52 is OFF, the switch portion 32 is capable of electrically disconnecting the clock generation portion 45 and the battery unit 13, making them a disconnected state.

In the present embodiment, the sensor circuit 33 is an example of a trigger portion that generates a trigger signal. In the present embodiment, the sensor circuit 33 receives electric power supply from the battery unit 13.

Next, the operation of the energy treatment device 11 of the present modified example will be explained. Similar to the first embodiment, by operating operation buttons 34A and 34B, the operator is capable of providing an ultrasonic energy, a high-frequency energy, or a heat energy to a treatment portion 24 to treat a treatment target region. In this used state, the switch portion 32 is in a connected state in which the battery unit 13 and a control circuit 31, or first to third amplifier circuits 26 to 28 are electrically connected. In the connected state, the sensor 47 senses an operator's hand gripping the energy treatment device 11, and, for example, provides a voltage that is higher than a reference value added to the other input terminal side to the one of the input terminals of the determination portion 52. Therefore, the determination portion 52 constantly transmits to the switch portion 32 a trigger signal (an ON output logic) for permitting a connected state.

In a case where the operator completes the treatment or temporarily stops the treatment, and the energy treatment device 11 is placed on a working table, etc., the sensor 47 does not provide voltage to the determination portion 52 since it does not sense a hand gripping the energy treatment device 11. Therefore, in the determination portion 52, as a result of a comparison with the reference value, the output logic is reversed and becomes OFF, thereby stopping the transmission of the trigger signal.

Therefore, the switch portion 32 makes the connection between the battery unit 13 and the control circuit 31, and the connection between the battery unit 13 and the first to third amplifier circuits 26 to 28 to be a disconnected state from the connected state. In this state, the energy treatment device 11 enters a power-saving mode (a standby mode) which suppresses power consumption. Only the sensor circuit 33 is connected to the battery unit 13 and receives electric power supply from the battery unit 13.

In a case where the operator grips the energy treatment device 11 again when the energy treatment device is in the power-saving mode, the sensor 47 sends a voltage higher than the reference value to the determination portion 52. At this time, the determination portion 52 transmits a trigger signal (an ON output logic) for permitting a connected state to the switch portion 32. The switch portion 32 switches all of the switches 32A from the disconnected state to a connected state. Therefore, the electric power is supplied to the control circuit 31, and the operation of an operation button 34 is validated. Therefore, the energy treatment device 11 transitions to an activation mode, in which it is fully activated, which allows the operator to operate a handle 35 and the operation button 34 to perform a desired treatment.

According to the present modified example, a power-saving energy treatment device 11 which is capable of preventing standby power from being consumed at the first to third amplifier circuits 26 to 28, the controller 46, and the clock generation portion 45, etc. can be provided.

In the present modified example, a visible light is used to detect the operator's gripping hand; however, a detection light used for detecting a hand is not limited to a visible light. As the detection light, (1) infrared rays (infrared lights) radiated from a human body can be used. Infrared lights may be detected by the sensor 47 provided in the housing 12 by providing a slit or a pin-hole on the housing 12. In this case, as the sensor 47, an infrared light detection sensor, that is, a MEMS non-contact infrared temperature sensor or an infrared light camera, etc., can be used.

As the detection light, (2) special lights of near-infrared lights or green lights (wavelength: 570 nm) can also be used. While these special lights have properties of being reflected by human skin, they have properties of being absorbed by hemoglobin inside the blood vessel. The special lights may be irradiated from a light-emitting diode or a lamp accommodated inside the housing 12. The sensor 47 is configured by light-receiving elements that can detect these special lights. In this example, the determination portion 52 determines whether or not a vein pattern detected by the sensor 47 matches a vein pattern of a general hand stored in the determination portion 52. In the case where the vein pattern detected by the sensor 47 matches the vein pattern of a hand, the determination portion 52 may recognize that the grip 22 is correctly gripped by the operator. In this case, the determination portion 52 transmits the trigger signal and allows the switch portion 32 to become a connected state. In the case where the vein pattern does not match, the switch portion 32 is made to become a disconnected state. According to this example, the sensor 47 can be prevented from a sensing error such as detecting the body of a patient.

Second Embodiment

Figure 9:
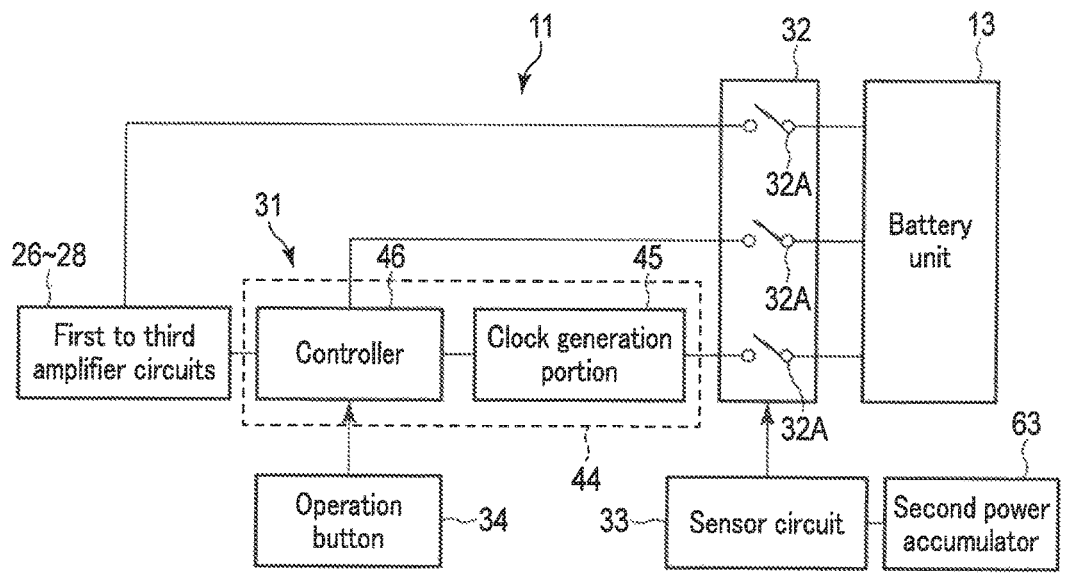
FIG. 9 is a schematic diagram showing configurations of a control circuit and a sensor circuit of an energy treatment device of a second embodiment.
Figure 10:
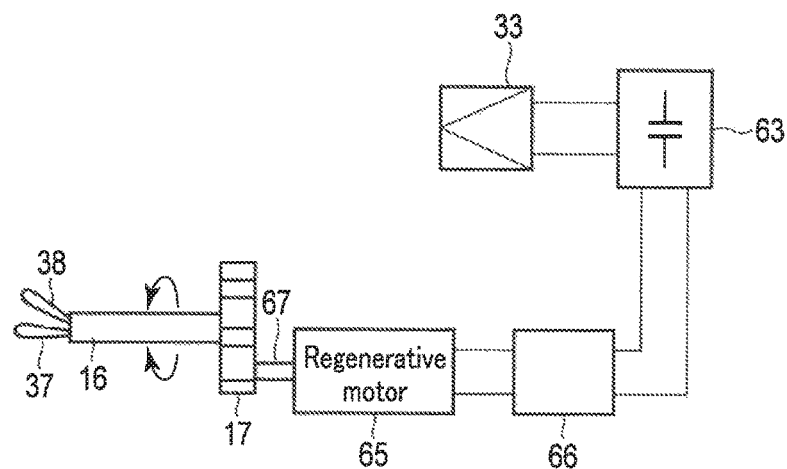
FIG. 10 is a schematic diagram explaining configurations of a power generation portion and a power conversion portion of the energy treatment device of the second embodiment shown in FIG. 9.

With reference to FIG. 9 and FIG. 10, a second embodiment of an energy treatment device will be explained. The energy treatment device 11 of the second embodiment differs from that of the first embodiment in that it comprises a second power accumulator 63 and a power generation portion 64. The other parts are identical to the first embodiment. Therefore, mainly the parts different from those of the first embodiment will be explained, and illustrations or explanations of the parts identical to those of the first embodiment will be omitted.

As shown in FIG. 9 and FIG. 10, the energy treatment device 11 comprises the second power accumulator 63 that supplies electric power to a sensor circuit 33, and the power generation portion 64 for generating power to be accumulated in the second power accumulator 63. The second power accumulator 63 is, for example, configured by a capacitor, and is capable of supplying electric power to the sensor circuit 33 (a trigger portion).

As shown in FIG. 10, the power generation portion 64 comprises a regenerative motor 65 (an energy conversion portion) and an electric power conversion portion 66. The regenerative motor 65 functions as a generator that generates electric power by receiving power (kinetic energy). The regenerative motor 65 is coupled to a revolving knob 17 via a shaft 67. The revolving knob 17 is an example of a moving region. When the revolving knob 17 is revolved about a central axis C, power is transmitted to the regenerative motor 65 via the shaft 67. When the power is transmitted to the regenerative motor 65, an electric power is generated at the regenerative motor 65. A power source (the moving region) of the power utilized for electric power generation at the regenerative motor 65 is not limited to the revolving knob 17. It may, for example, be a handle 35 (a movable handle) provided rotatably with respect to a housing 12.

The electric power conversion portion 66 is an electric power conversion circuit comprising an AC/DC converter and is electrically connected to the second power accumulator 63. The electric power conversion portion 66 commutes an alternating-current power generated at the regenerative motor 65 to a direct-current power, and converts it into a voltage that can be stored in the second power accumulator 63. That is, the electric power conversion portion 66 converts the alternating-current power generated at the regenerative motor 65 into a direct-current power having a voltage that can be stored in the second power accumulator 63. The power generation portion 64 may also be configured by a piezoelectric element (an energy conversion portion) that is provided inside an operation button 34, and generates electricity by a push operation of the operation button 34, and the electric power conversion portion 66 which converts the voltage generated at the piezoelectric element into a direct-current power having a voltage that can be stored in the second power accumulator 63. In this case, the operation button 34 becomes a moving region that moves with respect to the housing 12 in response to an operation input for supplying treatment energy to a treatment portion 24.

In the present embodiment, the sensor circuit 33 receives electric power supply from the second power accumulator 63. The configuration of the sensor circuit 33 is the same as that of the first embodiment.

When the sensor circuit 33 uses up the electric energy accumulated in the second power accumulator 63, the electric power supply to the sensor circuit 33 is automatically stopped, allowing the sensor circuit 33 to become a dormant state. When the sensor circuit 33 is in the dormant state, the energy treatment device 11 may have a second operation button 53 (an activation switch) to forcibly transition the energy treatment device 11 again to an activation mode. The configuration of the second operation button 53 is the same as that of a first modified example of a third embodiment described later on.

Furthermore, in order to reduce power consumption at the sensor circuit 33 when in a power-saving mode, the sensor circuit 33 may have a second switch portion that is configured by a relay circuit such as a semiconductor relay, etc. In this case, when a determination portion 52 does not transmit a trigger signal that permits connection between a clock generation portion 45 and a battery unit 13 within a certain time, the determination portion 52 may control the second switch portion to disconnect the sensor circuit 33 and the second power accumulator 63, thereby allowing the sensor circuit 33 to enter a dormant state. Accordingly, in this case, the sensor circuit 33 is driven only for a significantly short time. Also in the case of this example, it is preferred that the energy treatment device 11 has the second operation button 53 (the activation switch) for forcibly transitioning the energy treatment device 11 in the dormant state to the activation mode. The configuration of the second operation button 53 is the same as that of a first modified example of a third embodiment described later on. In the case where the second operation button 53 is operated to transition to the activation mode, the sensor circuit 33 also transitions to an activation state from the dormant state.

In the case where the energy treatment device 11 is in the activation mode, the sensor circuit 33 receives electric power supply from the second power accumulator 63; however, in the case where the electric energy accumulated in the second power accumulator 63 falls short, the sensor circuit 33 may also be configured to receive electric power supply from the battery unit 13 (a first power accumulator).

Next, the operation of the energy treatment device 11 of the present embodiment will be explained. Similar to the first embodiment, by operating operation buttons 34A and 34B, the operator is capable of providing an ultrasonic energy, a high-frequency energy, or a heat energy to a treatment portion 24 to treat a treatment target region. In this used state, the switch portion 32 is in a connected state, in which the battery unit 13 and a control circuit 31 or first to third amplifier circuits 26 to 28 are electrically connected. In this connected state, the determination portion 52 of the sensor circuit 33 transmits a trigger signal that permits a connected state to the switch portion 32 at regular intervals. In the power generation portion 64, the electric power generated at the regenerative motor 65 by the operation of the revolving knob 17 during treatment is accumulated in the second power accumulator 63.

In the case where the operator completes the treatment or temporarily stops the treatment, and the energy treatment device 11 is placed on a working table, etc., the sensor 47 sends temperature information of the energy treatment device 11 to the determination portion 52. Therefore, based on the temperature information, the determination portion 52 determines that the energy treatment device 11 is in an unused state, and stops transmitting the trigger signal. Therefore, the switch portion 32 makes the connection between the battery unit 13 and the control circuit 31, and the connection between the battery unit 13 and the first to third amplifier circuits 28 to be a disconnected state from the connected state. In this state, the energy treatment device 11 enters a power-saving mode (a standby mode) that suppresses power consumption. The sensor circuit 33 receives electric power supply from the second power accumulator 63.

In the power-saving mode, the determination portion 52 of the sensor circuit 33 is driven by a significantly smaller number of clocks than the number of clocks of the clock generation portion 45 of the control circuit 31. In a case where the sensor circuit 33 uses up the electric power of the second power accumulator 63, or in a case where the determination portion does not transmit a trigger signal within a predetermined time, the sensor circuit 33 becomes a dormant state in which power supply is stopped.

In a case where the operator grips the energy treatment device 11 again when the energy treatment device is in the power-saving mode, the temperature information of the energy treatment device 11 is sent to the determination portion 52. Therefore, based on the temperature information, the determination portion 52 determines that the energy treatment device 11 is in a used state, and transmits a trigger signal for permitting a connected state to the switch portion 32 at regular intervals. The switch portion 32 switches all of the switches 32A from the disconnected state to a connected state. Therefore, the electric power is supplied to the control circuit 31, and the operation of the operation button 34 is validated. Therefore, the energy treatment device 11 transitions to an activation mode, in which it is fully activated.

On the other hand, when the energy treatment device 11 is in a dormant state, the operator may press the second operation button 53 (the activation switch) to forcibly transition the energy treatment device 11 to an activation mode. In the activation mode, in the same manner as above, the operator is capable of operating the handle 35 or the operation button 34 to perform a desired treatment.

According to the present embodiment, the energy treatment device 11 comprises a housing 12 that can be held, a treatment portion 24 protruding from the housing 12, a moving region provided in a movable manner with respect to the housing 12, and moving with respect to the housing 12 based on one of an operation input for moving the treatment portion 24 and an operation input for supplying a treatment energy to the treatment portion 24, an energy conversion portion converting kinetic energy caused by the movement of the moving region into electric energy, and a second power accumulator 63 in which the electric energy converted at the energy conversion portion is accumulated, and which is connected to the trigger portion so that the electric energy is supplied to the trigger portion.

According to this configuration, by moving the moving region, the electric energy can be accumulated in the second power accumulator 63, and the accumulated electric energy can be supplied to the trigger portion. Therefore, the electric power of the battery unit 13 (the first power accumulator) can be prevented from being consumed at the trigger portion, and a power-saving energy treatment portion can be provided.

Third Embodiment

Figure 11:
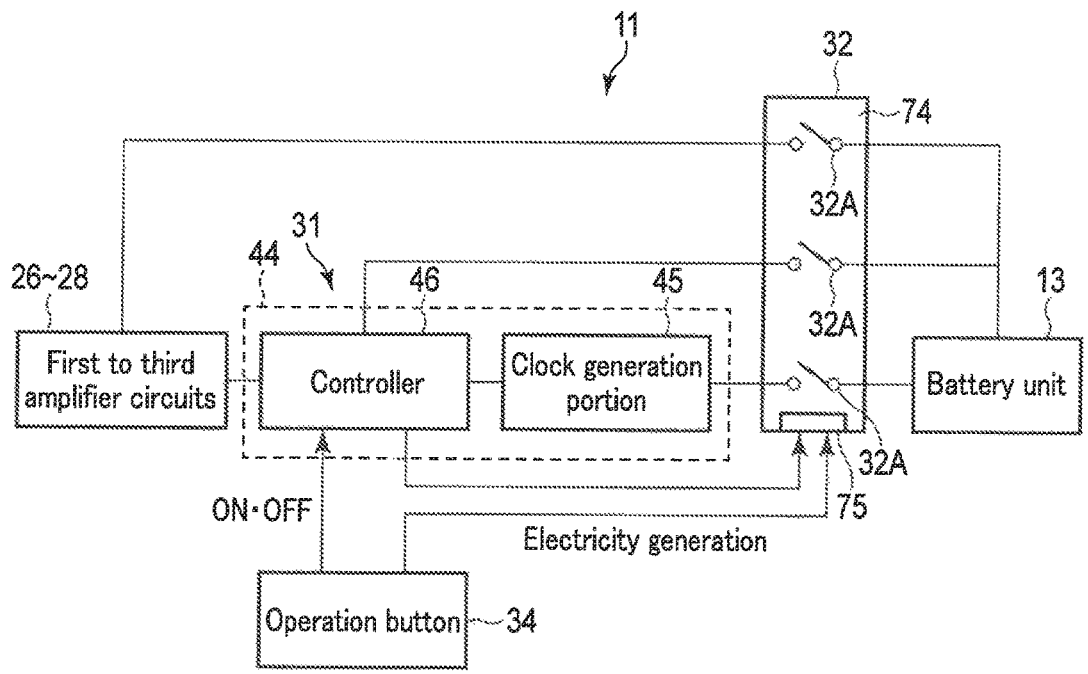
FIG. 11 is a block diagram explaining a control circuit and a configuration of the periphery thereof of an energy treatment device of a third embodiment.
Figure 12:
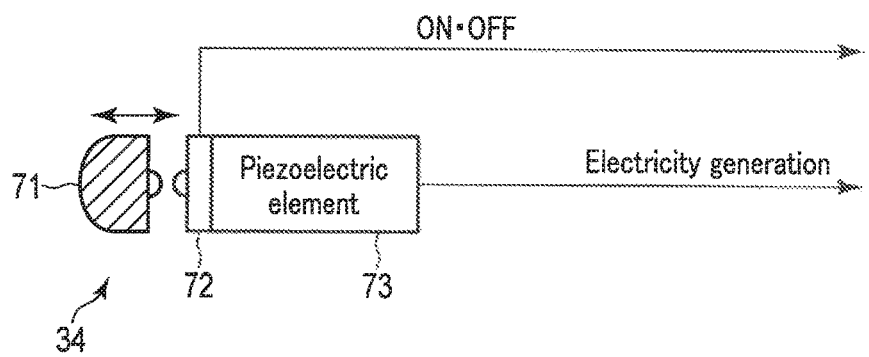
FIG. 12 is a schematic diagram explaining a configuration of an operation button of the energy treatment device shown in FIG. 11.

With reference to FIG. 11 and FIG. 12, a third embodiment of an energy treatment device 11 will be explained. The energy treatment device 11 of the third embodiment differs from that of the first embodiment in that it comprises a piezoelectric element adjacent to an operation button 34. The other parts are identical to the first embodiment. Therefore, mainly the parts different from those of the first embodiment will be explained, and illustrations or explanations of the parts identical to those of the first embodiment will be omitted.

As shown in FIG. 12, the operation button 34 comprises a button main body 71 that can be pressed towards the inner side of a housing 12 by a push from an operator, a detector 72 that detects the push of the button main body 71, and a piezoelectric element 73 provided adjacent to the detector 72, and generates electricity by the pushing pressure of the button main body 71. The detector 72 is connected to a controller 46 of a control circuit 31. The piezoelectric element 73 of the operation button 34 is an example of a trigger portion.

As shown in FIG. 11, a switch portion 32 has a switch portion main body 74 configured by a general relay circuit, and a switching controller 75 embedded inside the switch portion 32 so as to switch the switch portion main body 74 between a connected state and a disconnected state. The switching controller 75 is, for example, configured by a comparator, and outputs an ON output logic when electric power is supplied from the piezoelectric element 73 so as to switch the switch portion main body 74 from a disconnected state, in which a clock generation portion 45 and a battery unit 13 are electrically insulated, to a connected state, in which the clock generation portion 45 and the battery unit 13 are electrically connected. The switch portion 74 is preferred to be configured by, for example, a semiconductor relay (a photo MOS relay, a photocoupler, a FET, a transistor gate); however, may also be configured by a mechanical relay circuit.

The control circuit 31 comprises a CPU 44, a ROM, and a RAM, etc., and a motherboard (a substrate) that mounts them, and has wirings formed thereon to connect them to each other. The CPU 44 comprises a clock generation portion 45 for generating a clock signal, and a controller 46 (a main controller) that is activated by the clock signal generated by the clock generation portion 45, and mainly controls the first to third amplifier circuits 26 to 28. The controller 46 is connected to the switching controller 75 of the switch portion 32, and, when a control signal is not transmitted to the first to third amplifier circuits 26 to 28 for a predetermined time, controls the switching controller 75 to make the connection between the battery unit 13 and the clock generation portion 45 a disconnected state from the connected state.

Next, the operation of the energy treatment device 11 of the present embodiment will be explained. Similar to the first embodiment, by operating operation buttons 34A and 34B, the operator is capable of providing an ultrasonic energy, a high-frequency energy, or a heat energy to a treatment portion 24 to treat a treatment target region. In this used state, the switch portion 32 is in a connected state in which the battery unit 13, and the control circuit 31 or the first to third amplifier circuits 26 to 28, are electrically connected.

In the case where the operator completes the treatment or temporarily stops the treatment, and the energy treatment device 11 is placed on a working table, after a lapse of a predetermined time (after a lapse of several seconds to several minutes) from the last energy output, the controller 46 controls the switching controller 75 of the switch portion 32 to make the connection between the clock generation portion 45 and the battery unit 13 a disconnected state. In this state, the energy treatment device 11 enters a power-saving mode (a standby mode) that suppresses power consumption.

When the energy treatment device 11 is in the power-saving mode, in a case where the operator pushes the operation button 34, the piezoelectric element 73 of the operation button 34 is distorted, generating electricity, and supplies an electric current (a trigger signal) to the switching controller 75 of the switch portion 32. At this time, the switching controller 75 switches all of the switches 32A of the switch portion main body 74 from the disconnected state to a connected state. Therefore, the electric power is supplied to the control circuit 31, and the operation of the operation button 34 is validated. Therefore, the energy treatment device 11 transitions to an activation mode, in which it is fully activated. In the activation mode, by pressing down the operation button 34 again, the operator is able to provide various energies to a treatment target region.

According to the present embodiment, the trigger portion is provided on the operation button 34, and generates the trigger signal in tandem with the operation carried out with respect to the operation button 34. This configuration allows a sensor circuit 33 to be omitted. Therefore, electric power supply to the sensor circuit 33 becomes unnecessary, and, in comparison to the first embodiment and the second embodiment, a further power-saved energy treatment device 11 can be provided.

In the present embodiment, the trigger portion is configured by the piezoelectric element 73 that converts the pushing pressure with respect to the operation button 34 into electric power, and generates the trigger signal. According to this configuration, a simple structure can provide a power-saving energy treatment device 11.

(First Modified Example of Third Embodiment)

With reference to FIG. 13, a first modified example of the energy treatment device of the third embodiment will be explained. An energy treatment device 11 of the first modified example of the third embodiment differs from that of the third embodiment in that it comprises a second operation button 53 for allowing the energy treatment device 11 to enter an activation mode from a power-saving mode separately from an operation button 34. The other parts are identical to the third embodiment. Therefore, mainly the parts different from those of the third embodiment will be explained, and illustrations or explanations of the parts identical to those of the third embodiment will be omitted.

The energy treatment device 11 comprises the second operation button 53, which is provided at a position near a grip 22, and can be pushed towards the inside of a housing 12. The second operation button 53 is a switch for activation, which is exclusively used for the energy treatment device 11 to transition from a power-saving mode to an activation mode. The second operation button 53 is connected to a switching controller 75 of a switch portion 32 via an electric wiring.

The second operation button 53 has a structure in which the detector 72 is omitted from the operation button 34 shown in FIG. 12 of the third embodiment. That is, when an operator presses down the second operation button 53, a piezoelectric element 73 is distorted, causing electricity to be generated, which allows an electric current (a trigger signal) to flow to the switching controller 75 of the switch portion 32. The second operation button 53 is an example of a trigger portion that transmits a trigger signal.

Next, the operation of the energy treatment device of the present modified example will be explained. Similar to the first embodiment, by operating operation buttons 34A and 34B, an operator is capable of providing an ultrasonic energy, a high-frequency energy, or a heat energy to a treatment portion to treat a treatment target region. In this used state, the switch portion 32 is in a connected state, in which a battery unit 13 and a control circuit 31 or first to third amplifier circuits 26 to 28 are electrically connected.

In the case where the operator completes the treatment or temporarily stops the treatment, and the energy treatment device 11 is placed on a working table, after a lapse of a predetermined time (after a lapse of several seconds to several minutes) from the last energy output, a controller 46 controls the switching controller 75 of the switch portion 32 to make the connection between a clock generation portion 45 and the battery unit 13 a disconnected state. In this state, the energy treatment device 11 enters a power-saving mode (a standby mode) that suppresses power consumption.

When the energy treatment device 11 is in the power-saving mode, in a case where the operator pushes the second operation button 53, the piezoelectric element 73 of the second operation button 53 generates electricity and supplies an electric current (a trigger signal) to the switch portion 32.

At this time, the switching controller 75 switches all of the switches 32A of a switch portion main body 74 from the disconnected state to a connected state. Therefore, electric power is supplied to the control circuit 31, and the operation of the operation button 34 is validated. Therefore, the energy treatment device 11 transitions to an activation mode in which it is fully activated. In the activation mode, by pressing down the operation button 34 again, the operator is able to provide various energies to the treatment target region.

According to the present modified example, the trigger portion is provided on the second operation button 53 that is different from the operation button 34, and generates the trigger signal in tandem with the operation carried out with respect to the second operation button 53. This configuration allows an exclusive switch for transitioning the switch portion to a connected state (an activation state) to be provided separately from the operation button 34, thereby improving convenience and operability for the operator.

The present invention is not limited to the above-described embodiments, and can be modified as appropriate in practice without departing from the gist of the invention. In other words, although the switch portion 32 is described in the present embodiment as being in a connected state when there is a trigger signal from the determination portion 52, these combinations are an example, and the switch portion 32 may, of course, instead be in a connected state when there is no trigger signal. In addition, it is, of course, possible to combine the energy treatment devices 11 of each of the above embodiments to configure one energy treatment device 11.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

The invention claimed is:

1. An energy treatment device comprising:
   a first power accumulator that accumulates electric power;
   a clock generation portion that generates a clock signal based on the electric power;
   a controller that uses the clock signal to control supply of an energy to be used for treatment at a treatment portion;
   a memory that stores threshold information;
   a trigger portion that generates a trigger signal that permits the clock generation portion and the first power accumulator to be electrically connected so that the controller receives the clock signal;
   a switching portion that, in accordance with a presence or absence of the trigger signal at the trigger portion, switches between a connected state in which the clock generation portion and the first power accumulator are electrically connected, and a disconnected state in which the clock generation portion and the first power accumulator are electrically separated;
   a housing, the treatment portion protruding from the housing;
   a moving region that is configured to move relative to the housing; and
   an energy conversion portion that converts kinetic energy, caused by movement of the moving region, into electric energy, the energy conversion portion being connected to the trigger portion;
   wherein:
   the trigger portion includes:
      a sensor that senses a temperature of the housing; and
      a determination portion that is configured to generate and transmit the trigger signal to the switching portion when the temperature is equal to or higher than the threshold information; and
   upon receiving the trigger signal, the switching portion is configured to automatically switch from the disconnected state to the connected state.

2. The energy treatment device according to claim 1, further comprising an operation button that turns ON/OFF supply of an energy to be used for treatment at the treatment portion,
   wherein an operation with respect to the operation button becomes valid after the first power accumulator and the clock generation portion are electrically connected by the switching portion.

3. The energy treatment device according to claim 1, further comprising an operation button that turns ON/OFF supply of an energy to be used for treatment at the treatment portion,
   wherein the trigger portion is provided on the operation button, and generates the trigger signal in accordance with an operation with respect to the operation button.

4. The energy treatment device according to claim 3, wherein the trigger portion is configured by a piezoelectric element that converts a pushing pressure with respect to the operation button into electric power to generate the trigger signal.

5. The energy treatment device according to claim 1, wherein the switching portion switches to the first disconnected state in a case where the trigger signal is not generated from the trigger portion, and switches to the first connected state in a case where the trigger signal is generated from the trigger portion.

6. The energy treatment device according to claim 1, wherein the trigger portion comprises a sensor, and a determination portion that determines one of a used state and an unused state based on a detection result detected at the sensor, and generates the trigger signal when in the used state.

7. The energy treatment device according to claim 6, wherein the trigger portion is driven by a smaller number of clocks than a number of clocks of the clock generation portion.

8. The energy treatment device according to claim 1, further comprising an operation button that turns ON/OFF supply of an energy to be used for treatment at the treatment portion,
   wherein the trigger portion is provided on a second operation button that is different from the operation button, and generates the trigger signal in accordance with an operation with respect to the second operation button.

9. The energy treatment device according to claim 1, wherein the switching portion includes a switch, the switch being located between the controller and the first power accumulator, and a third switch switching, in accordance with the presence/absence of the trigger signal at the trigger portion, between a third connected state, where the controller and the first power accumulator are electrically connected, and a third disconnected state, where the controller and the first power accumulator are electrically separated.

10. The energy treatment device according to claim 1, wherein a kinetic energy caused by moving the moving region that moves with respect to the housing is converted into an electric energy, and the trigger signal is generated from the trigger portion based on the electric energy.

11. The energy treatment device according to claim 1, further comprising a second power accumulator, wherein the electric energy that is converted from the kinetic energy at the energy conversion portion is accumulated in the second power accumulator and supplied to the trigger portion.

12. The energy treatment device according to claim 1, wherein the housing comprises a housing main body and a grip that extends from the housing main body towards a direction intersecting a central axis of the housing main body, and the sensor is provided at a position on the grip.

13. The energy treatment device according to claim 11, wherein:
 the moving region includes a revolving knob that is configured to revolve together with the treatment portion relative to the housing, and
 the energy conversion portion includes a regenerative motor that is configured to generate the electric energy by transmitting the kinetic energy from the revolving knob.

* * * * *